United States Patent
Kodama et al.

(10) Patent No.: US 12,161,768 B2
(45) Date of Patent: Dec. 10, 2024

(54) ULTRAVIOLET IRRADIATION APPARATUS AND ULTRAVIOLET IRRADIATION METHOD

(71) Applicant: ASAHI KASEI KABUSHIKI KAISHA, Tokyo (JP)

(72) Inventors: Atsushi Kodama, Tokyo (JP); Sho Sugiyama, Tokyo (JP); Hiroyuki Kishi, Tokyo (JP); Naoto Ito, Tokyo (JP); Sumire Jinno, Tokyo (JP); Ryosuke Baba, Tokyo (JP); Suguru Ando, Tokyo (JP); Hiroshi Chiba, Tokyo (JP)

(73) Assignee: Asahi Kasei Kabushiki Kaisha, Tokyo (JP)

(*) Notice: Subject to any disclaimer, the term of this patent is extended or adjusted under 35 U.S.C. 154(b) by 438 days.

(21) Appl. No.: 17/630,409

(22) PCT Filed: Jul. 30, 2020

(86) PCT No.: PCT/JP2020/029344
§ 371 (c)(1),
(2) Date: Jan. 26, 2022

(87) PCT Pub. No.: WO2021/020536
PCT Pub. Date: Feb. 4, 2021

(65) Prior Publication Data
US 2022/0280666 A1     Sep. 8, 2022

(30) Foreign Application Priority Data

Jul. 31, 2019 (JP) .................................. 2019-141630
Jul. 31, 2019 (JP) .................................. 2019-141631

(51) Int. Cl.
*A61L 2/10* (2006.01)
*A61L 2/26* (2006.01)
*C02F 1/32* (2023.01)

(52) U.S. Cl.
CPC .............. *A61L 2/10* (2013.01); *A61L 2/26* (2013.01); *C02F 1/325* (2013.01); *A61L 2202/122* (2013.01)

(58) Field of Classification Search
CPC ........ A61L 2/10; A61L 2/26; A61L 2202/122; A61L 2/0047; A61L 2202/11;
(Continued)

(56) References Cited

U.S. PATENT DOCUMENTS 7,250,610 B1    7/2007   Cox et al.
10,780,188 B2 *   9/2020   Kishi ..................... B32B 5/026
(Continued)

FOREIGN PATENT DOCUMENTS

CN    104159851 B  *  6/2016 ............. C02F 1/325
CN    108136060 A    6/2018
(Continued)

OTHER PUBLICATIONS

English translation of publication CN-104159851-B, published Jun. 8, 2016. (Year: 2016).*

(Continued)

*Primary Examiner* — Joseph W Drodge
(74) *Attorney, Agent, or Firm* — Morgan, Lewis & Bockius LLP

(57) ABSTRACT

An ultraviolet irradiation device includes an inner cylinder forming a treatment flow path, an inflow portion allowing the object to flow into the treatment flow path, an outer cylinder accommodating the inner cylinder, a light emitting element irradiating the object passing through the treatment flow path with ultraviolet light, an O-ring dividing a space provided between an outer circumferential surface of the inner cylinder and an inner circumferential surface of the outer cylinder into a first chamber through which the object before ultraviolet irradiation passes and a third chamber (Continued)

through which the object after the ultraviolet irradiation passes, and a second chamber communicating with the first chamber through communication holes. The second chamber communicates with the treatment flow path through a plate.

27 Claims, 10 Drawing Sheets

(58) Field of Classification Search
CPC ........ A61L 2209/12; A61L 9/20; C02F 1/325; C02F 2201/3222; C02F 2201/3228; C02F 2201/328; C02F 1/32; C02F 2201/32; C02F 2201/3225; B01J 19/123; B01J 2219/1233
See application file for complete search history.

(56) References Cited

U.S. PATENT DOCUMENTS

| | | | |
|---|---|---|---|
| 11,464,885 B2 * | 10/2022 | Kodama | .................. C02F 1/325 |
| 2007/0125960 A1 | 6/2007 | Chen | |
| 2012/0318749 A1 | 12/2012 | Stokes et al. | |
| 2013/0119266 A1 | 5/2013 | Mondt | |
| 2014/0240695 A1 | 8/2014 | Pagan et al. | |
| 2015/0114912 A1 | 4/2015 | Taghipour | |
| 2017/0290943 A1 | 10/2017 | Stokes et al. | |
| 2018/0140729 A1 | 5/2018 | Kiuchi et al. | |
| 2018/0147314 A1 | 5/2018 | Stokes et al. | |
| 2018/0228928 A1 | 8/2018 | Ochi et al. | |
| 2018/0244543 A1 | 8/2018 | Ochi et al. | |
| 2018/0257953 A1 * | 9/2018 | Mochizuki | ................ A61L 9/20 |
| 2018/0370821 A1 | 12/2018 | Kishi et al. | |
| 2019/0184045 A1 | 6/2019 | Mochizuki et al. | |
| 2019/0256379 A1 | 8/2019 | Kato | |
| 2019/0256380 A1 | 8/2019 | Ochi et al. | |
| 2019/0298868 A1 * | 10/2019 | Kishi | ........................ A61L 2/10 |
| 2019/0321505 A1 * | 10/2019 | Kodama | .................... C02F 1/32 |
| 2019/0322546 A1 * | 10/2019 | Sugiyama | ................ A61L 2/10 |
| 2020/0002191 A1 | 1/2020 | Mochizuki | |
| 2021/0070632 A1 | 3/2021 | Mochizuki | |

FOREIGN PATENT DOCUMENTS

| | | |
|---|---|---|
| CN | 109069674 A | 12/2018 |
| CN | 109133260 A | 1/2019 |
| CN | 208732674 U | 4/2019 |
| CN | 109790051 A | 5/2019 |
| EP | 3756694 A1 | 12/2020 |
| JP | H02108789 U | 8/1990 |
| JP | 2013536003 A | 9/2013 |
| JP | 5432286 B2 | 3/2014 |
| JP | 6080937 B1 | 2/2017 |
| JP | 2017087104 A | 5/2017 |
| JP | 2018008213 A | 1/2018 |
| JP | 2018140380 A | 9/2018 |
| JP | 6404404 B1 | 10/2018 |
| JP | 2018/202205 A | 12/2018 |
| JP | 2019098055 A | 6/2019 |
| JP | 2019141292 A | 8/2019 |
| JP | 2019187656 A | 10/2019 |
| JP | 2019201862 A | 11/2019 |
| WO | 2005105675 A1 | 11/2005 |
| WO | 2019049702 A1 | 8/2020 |

OTHER PUBLICATIONS

Supplemental European Search Report, European Patent Application No. 20846666.4, dated Aug. 12, 2022, 4 pages.
European Office Action, European Patent Application No. 20846666.4, dated Aug. 24, 2022, 5 pages.
Machine English Translation for JP2018-008213A, 20 pages.
International Preliminary Report on Patentability for corresponding International Application No. PCT/JP2020/029344 dated Feb. 1, 2022, 6 pages.
Notification of Transmittal of Copies of Translation of the International Preliminary Report on Patentability (Chapter 1) for corresponding International Application No. PCT/JP2020/029344 dated Feb. 10, 2022, 1 page.
International Search Report and Written Opinion issued in corresponding International Patent Application No. PCT/JP2020/029344 dated Feb. 4, 2021, 9 pages.

* cited by examiner

FIG. 5A
FIG. 5B
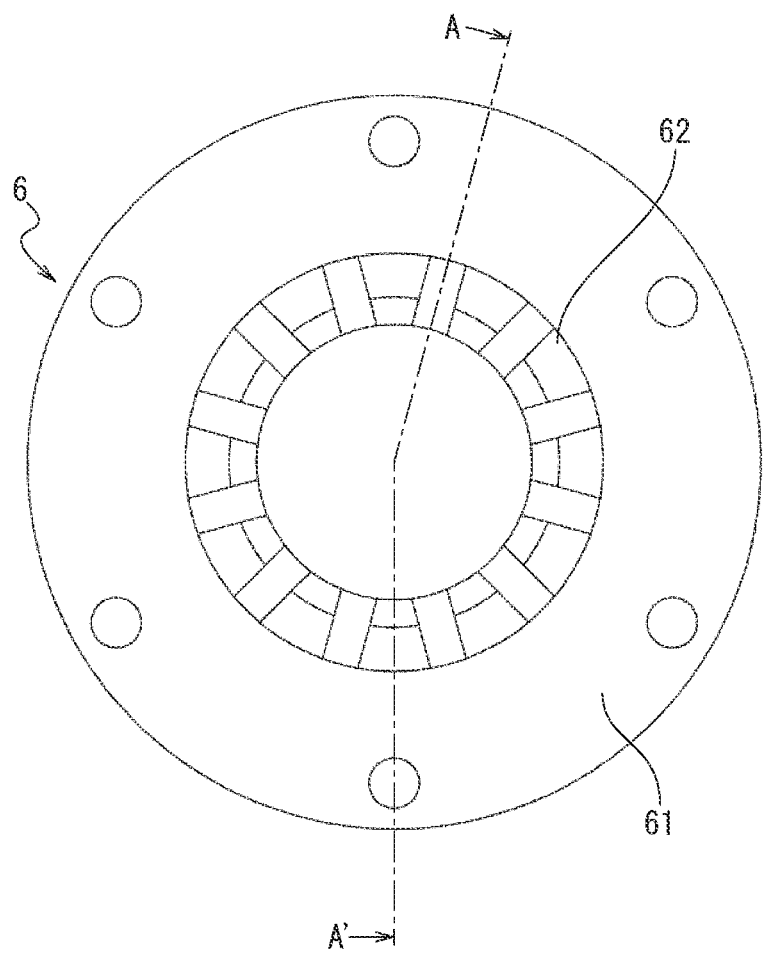
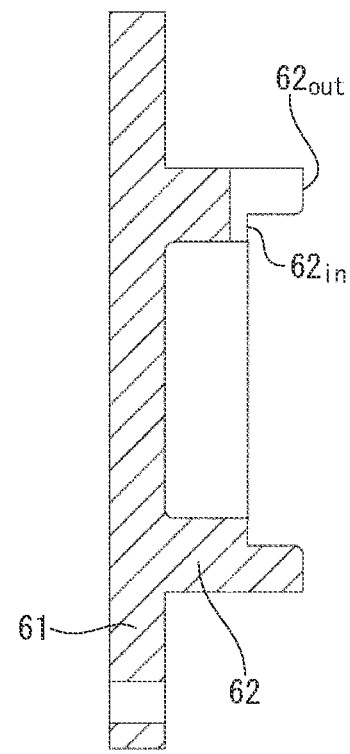

ULTRAVIOLET IRRADIATION APPARATUS AND ULTRAVIOLET IRRADIATION METHOD

RELATED APPLICATIONS

This application is the U.S. national stage application of International (PCT) Patent Application Serial No. PCT/JP2020/029344, filed Jul. 30, 2020, which claims the benefit of Japanese Application No. JP 2019-141630, filed Jul. 31, 2019, and Japanese Application No. JP 2019-141631, filed Jul. 31, 2019. The entire disclosure of each of these applications is hereby incorporated by reference.

TECHNICAL FIELD

The present invention relates to an ultraviolet irradiation apparatus and an ultraviolet irradiation method.

BACKGROUND ART

Conventionally, irradiation devices such as sterilization devices using ultraviolet light have used tubes such as mercury lamps or xenon lamps as ultraviolet light sources. Additionally, in recent years, the practical use of LEDs (light emitting diodes) that can emit wavelengths enabling sterilization has allowed for realization of device configurations that could not be achieved by such devices using tubes as ultraviolet light sources. An example of irradiation devices using LEDs that have been proposed is an irradiation device in which an object to be irradiated is introduced into an integrating sphere, made to pass through a hollow portion of the integrating sphere, and irradiated with ultraviolet light in the hollow portion (for example, see PTL 1). In other proposed irradiation devices that are configured to emit ultraviolet light along a longitudinal direction toward a fluid flowing through a straight pipe that forms a longitudinally extending flow path, the flow velocity of the fluid in the flow path pipe is adjusted by devising a structure for allowing the fluid to flow into the flow path pipe or a structure for allowing the fluid to flow out from the flow path pipe (for example, see PTL 2 and 3).

CITATION LIST

Patent Literature

PTL 1: JP 5432286 B
PTL 2: JP 6080937 B
PTL 3: JP 6404404 B

SUMMARY OF INVENTION

Technical Problem

However, in the irradiation device using the hollow portion of the integrating sphere as a treatment flow path for ultraviolet irradiation, the treatment flow path is surrounded by a curved surface, so that it is necessary to process the hollow portion into a complicated shape. Additionally, since there are few materials with high durability against ultraviolet light and excellent processability, the device is inferior in terms of industrial economic efficiency. Furthermore, in such irradiation devices that perform ultraviolet irradiation using a straight pipe, polytetrafluoroethylene (PTFE) is often used as the material of the irradiation devices. However, PTFE is a material that is relatively low in water pressure resistance and easily causes plastic deformation and creep rupture at contact points with other materials, and there is also a concern about durability.

In an irradiation device having a treatment flow path made of PTFE, a highly strong case unit is needed outside the treatment flow path when water pressure resistance is required. However, providing the case unit limits the structure of an irradiation area and a method for manufacturing the irradiation area, and it is difficult to manufacture an irradiation device having low inter-individual variability and excellent robustness.

Additionally, in a device that irradiates a fluid with ultraviolet light, improving irradiation efficiency requires controlling the flow of the fluid in a treatment flow path so that flow velocity distribution matches ultraviolet flux distribution in the treatment flow path.

PTL 2 proposes a module structure in which an inflow port and a treatment flow path communicate with each other through a gap between a light source-side end portion of the treatment flow path and a member facing the light source-side end portion. However, when the gap between the light source-side end portion and the member facing the light source-side end portion is set small, a slight assembly dimensional error may cause a velocity difference in flow velocity, which may result in the occurrence of an insufficiently irradiated region. Conversely, when the gap is set large, a velocity difference due to inertia of the fluid cannot be sufficiently reduced, and it is therefore difficult to ensure uniformity of the flow in the treatment flow path.

Additionally, PTL 3 proposes a module structure in which a communication path to a treatment flow path includes an annular narrow path formed by making the communication path narrower. However, since the structure depends on flow velocity control by gaps, a slight assembly dimensional error causes a velocity difference in flow velocity, as described above, which deteriorates rectification effect. Additionally, forming the narrow path causes a problem of increased pressure loss in the entire irradiation device.

Accordingly, the present invention has been made in view of the above conventional unsolved problems, and it is an object of the present invention to provide an ultraviolet irradiation device and an ultraviolet irradiation method that achieve excellent robustness, ensure uniformity of flow in a treatment flow path, and can suppress pressure loss in the entire ultraviolet irradiation device without causing unintentional leakage of an object to be irradiated, such as fluid, even when assembly accuracy is low.

Solution to Problem

According to an aspect of the present invention, there is provided an ultraviolet irradiation device including: a cylindrical portion configured to form a cylindrical treatment flow path extending in a longitudinal direction and have at least one open end; an inflow portion configured to allow an object to flow into the treatment flow path from the open end side of the cylindrical portion; a light emitting element provided at least one end of the cylindrical portion and configured to irradiate the object passing through the treatment flow path with ultraviolet light; an outer cylinder configured to accommodate the cylindrical portion, in which a space is provided between an outer circumferential surface of the cylindrical portion and an inner circumferential surface of the outer cylinder; a dividing member in which at least a portion in contact with the outer circumferential surface of the cylindrical portion and a portion in contact with the inner circumferential surface of the outer cylinder are made of an elastic member, the dividing member dividing the space into an inflow-side region through which the object before being irradiated with the ultraviolet light passes and an outflow-side region through which the object after being irradiated with the ultraviolet light passes; and a retention portion configured to communicate with the inflow-side region through a first communication portion, wherein the inflow-side region communicates with the inflow portion, and the retention portion and the treatment flow path communicate with each other through a second communication portion.

According to another aspect of the present invention, there is provided an ultraviolet irradiation method configured to allow an object to flow from an inflow portion into a treatment flow path formed inside a cylindrical portion having one open end and extending in a longitudinal direction and irradiating the object passing through the treatment flow path with ultraviolet light, the method including: interposing, between an outer circumferential surface of the cylindrical portion and an inner circumferential surface of an outer cylinder accommodating the cylindrical portion, a dividing member in which at least a portion in contact with the outer circumferential surface of the cylindrical portion and a portion in contact with the inner circumferential surface of the outer cylinder are made of an elastic member, the dividing member dividing into two regions; using a region of the two regions on the open end side of the cylindrical portion as an inflow-side region through which the object before being irradiated with the ultraviolet light passes and interposing the inflow-side region and a retention portion downstream the inflow-side region in a flow path of the object from the inflow portion to the treatment flow path; and allowing the object to pass through the inflow-side region and the retention portion and then flow into the treatment flow path.

In addition, according to another aspect of the present invention, there is provided an ultraviolet irradiation method configured to allow an object to flow from an inflow portion into a cylindrical treatment flow path extending in a longitudinal direction and irradiate the object passing through the treatment flow path with ultraviolet light, the method including: providing a plurality of communication portions formed with a plurality of communication holes in a flow path of the object from the inflow portion to the treatment flow path; and allowing the object to pass through the plurality of communication portions and then flow into the treatment flow path.

Advantageous Effects of Invention

According to the one aspect of the present invention, even when assembly accuracy is low, the rectification effect can be further improved, as a result of which uniformity of the flow in the treatment flow path can be ensured, and pressure loss can be suppressed.

BRIEF DESCRIPTION OF DRAWINGS

FIG. 5A is a top view of the lid unit, and FIG. 5B is a cross sectional view;

DESCRIPTION OF EMBODIMENTS

Figure 1:
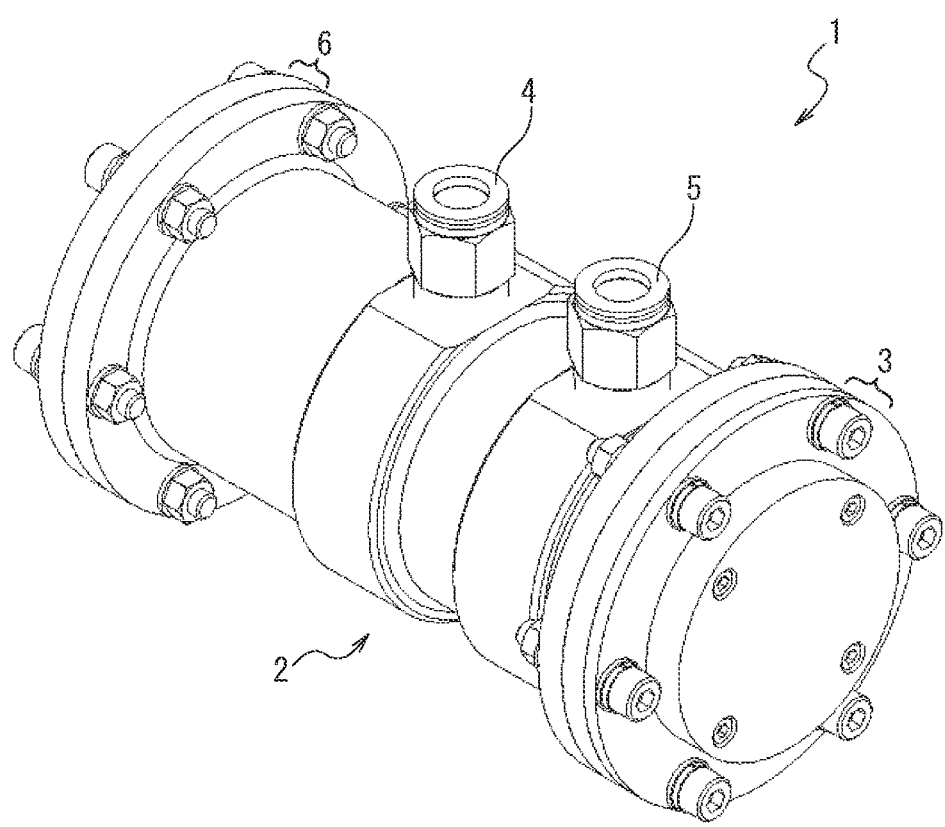
FIG. 1 is a perspective view illustrating one example of an ultraviolet irradiation device according to the present invention.

Next, referring to the drawings, an embodiment of the present invention will be described. In the description of the drawings, same or similar elements are denoted by the same or similar reference signs. The drawings are schematic and relations between thicknesses and two-dimensional dimensions, ratios between thicknesses of respective layers, and the like may be different from actual ones. The embodiments to be described below are intended to exemplify a device and a method for embodying the technical idea of the present invention, and the technical idea of the present invention does not limit materials, shapes, structures, arrangements, and the like of components to those described below. Various modifications may be made to the technical idea of the present invention within the technical scope defined by the claims.

<Configuration of Ultraviolet Irradiation Device>

Figure 2:
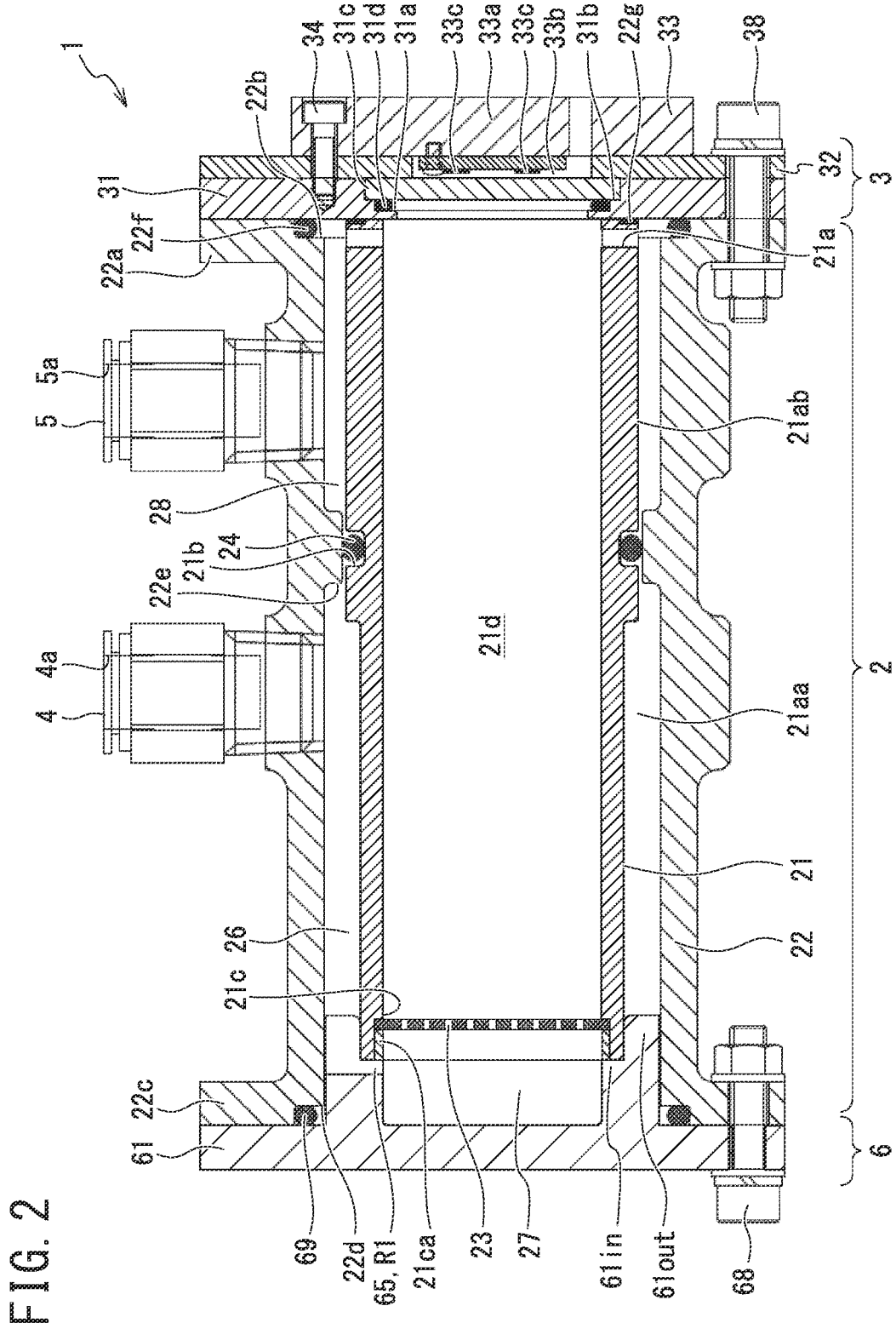
FIG. 2 is a longitudinal cross sectional view of the ultraviolet irradiation device.

FIG. 1 is a perspective view illustrating one example of an appearance of an ultraviolet irradiation device 1 to which the present invention is applied, and FIG. 2 is a longitudinal cross sectional view of the ultraviolet irradiation device 1.

As illustrated in FIG. 1, the ultraviolet irradiation device 1 includes a sterilization treatment unit 2, a light emission unit 3, an inflow portion 4, an outflow portion 5, and a lid unit 6.

As illustrated in FIG. 2, the sterilization treatment unit 2 has a double-tube structure including an inner cylinder (cylindrical portion) 21, an outer cylinder 22 accommodating the inner cylinder 21, a circular plate 23 fixed to an opening portion on one end side of the inner cylinder 21 and being for rectifying a fluid flown into the inner cylinder 21, and an O-ring (dividing member) 24 arranged between the inner cylinder 21 and the outer cylinder 22 and dividing a gap between the inner cylinder 21 and the outer cylinder 22.

The inner cylinder 21 has a tubular shape having a circular cross section with both ends open, and includes a small diameter portion 21*aa* and a large diameter portion 21*ab* continuous with the small diameter portion 21*aa* and having a larger outer diameter than the small diameter portion. The inner cylinder 21 has a constant inner diameter.

The inner cylinder 21 has an inner wall made of an ultraviolet reflective material, and the ultraviolet reflective material has a total reflectance of from 80% to 99% in the ultraviolet region. Examples of the ultraviolet reflective material applied to the inner cylinder 21 include polytetrafluoroethylene (PTFE) and the like.

At positions close to an end portion of the inner cylinder 21 on the light emission unit 3 side are formed communication ports 21a oriented in a radial direction and penetrating the inner cylinder 21, for example, at six locations separated by 60 degrees in a circumferential direction.

Note that the positions and number of the communication ports 21a arranged are not limited thereto.

Although the shape of the communication ports 21a is preferably circular in cross section from the viewpoint of machining, the shape thereof is not limited to a circular cross section, and can be any shape. The communication ports 21a are preferably arranged at positions slightly deviated from an end portion of the treatment flow path 21d on the light emission unit 3 side toward an end portion thereof opposite to the light emission unit 3.

A groove 21b is formed on an outer circumferential surface of the large diameter portion 21ab of the inner cylinder 21, which is a substantially center part in a direction in which the inner cylinder 21 extends. The groove 21b has, for example, a rectangular cross section.

A stepped portion 21c that fits with the plate 23 is formed on an inner circumferential surface of an end portion of the inner cylinder 21 opposite to the light emission unit 3. The inner diameter of the stepped portion 21c coincides with the diameter of the plate 23. The plate 23 is fixed to the inner cylinder 21 by fitting an annular member 21ca having a circular annular shape whose inner diameter is the same as the inner diameter of the treatment flow path 21d and whose outer diameter coincides with the inner diameter of the stepped portion 21c into the stepped portion 21c so as to sandwich the plate 23 with the plate 23 placed in the stepped portion 21c.

Additionally, a hollow portion of the inner cylinder 21 forms the treatment flow path 21d. Since the inner wall of the inner cylinder 21 is made of an ultraviolet reflective material, ultraviolet light can be efficiently applied to an object passing through the treatment flow path 21d.

The outer cylinder 22 is made of, for example, polyolefin, specifically, polypropylene or polyethylene, and has a tubular shape having both ends open and a circular cross section. A flange portion 22a is formed on an outer circumferential surface of an end portion of the outer cylinder 22 on the light emission unit 3 side, and a stepped portion 22b is formed on an inner circumferential surface of an end portion of the outer cylinder 22 on the flange portion 22a side. Similarly, a flange portion 22c is formed on an outer circumferential surface of an end portion of the outer cylinder 22 on the lid unit 6 side, and a stepped portion 22d is formed on an inner circumferential surface of an end portion of the outer cylinder 22 on the flange portion 22c side.

A protrusion 22e having a circular annular shape is formed on an inner circumferential surface of a substantially center part of a longitudinal direction of the outer cylinder 22. The protrusion 22e is formed so that the outer circumference of the large diameter portion 21ab of the inner cylinder 21 and an inner circumference of the protrusion 22e are in close contact with each other when the ultraviolet irradiation device 1 is assembled. Then, by inserting the inner cylinder 21 into the outer cylinder 22 with the O-ring 24 made of an elastic member fitted into the groove 21b formed in the inner cylinder 21, the gap formed between the inner cylinder 21 and the outer cylinder 22 is divided into two regions by the protrusion 22e. The O-ring 24 has a shape that comes into close contact with the inner cylinder 21 and the outer cylinder 22 due to a radial wall thickness thereof, and divides so that the object does not go back and forth between the small diameter portion 21aa side and the large diameter portion 21ab side of the inner cylinder 21 in the gap between the inner cylinder 21 and the outer cylinder 22.

In this case, as illustrated in FIG. 2, the outer cylinder 22 is provided with the protrusion 22e, and the outer cylinder 22 comes in contact with the inner cylinder 21 at the protrusion 22e through the O-ring 24. Specifically, a part of the outer cylinder 22 in contact with the O-ring 24 has an inner diameter smaller than an inner diameter of the other part thereof excluding the part in contact with the O-ring 24. Therefore, using an O-ring having a smaller outer diameter (hereinafter also referred to as small-sized O-ring) as the O-ring 24 interposed between the outer cylinder 22 and the inner cylinder 21 allows the gap between the inner and outer cylinders 21 and 22 to be divided. Here, in order to improve rectification effect, it is necessary to widen the gap between the inner cylinder 21 and the outer cylinder 22. However, even when widening the gap between the inner and outer cylinders 21 and 22 in this way, providing the protrusion 22e on the outer cylinder 22 allows even a relatively small sized O-ring to be applied as the O-ring 24 as long as it satisfies accuracy and durability. From the viewpoint of sealability, the O-ring 24 is preferably a member that has elasticity at least in portions in contact with the inner and outer cylinders 21 and 22. Examples of such a member include flexible and highly structure-following materials, such as elastomers.

Note that although the above description has described the case where the gap between the inner and outer cylinders 21 and 22 is divided into the two regions: the small diameter portion 21aa side and the large diameter portion 21ab side by the protrusion 22e and the O-ring 24 fitted into the groove 21b, the present invention is not limited thereto. For example, it suffices that the gap between the inner and outer cylinders 21 and 22 can be watertightly divided into the two regions by interposing an elastic member having a circular annular shape or by other means.

In addition, the outer cylinder 22 is not limited to the tubular member with both ends open, and may be a tubular member with at least one end open. By opening both ends of the outer cylinder 22, more light emission units or lid units different in shape and design content can be applied as the light emission unit 3 or the lid unit 6. Thus, it is possible to realize more ultraviolet irradiation devices 1 having different shapes for one designed outer cylinder 22. In other words, versatility can be improved.

At a portion of the outer cylinder 22 facing the small diameter portion 21aa of the inner cylinder 21, the inflow portion 4 projecting to the outer circumferential side and having a cylindrical hollow portion thereinside is integrally formed with the outer cylinder 22. At a portion of the outer cylinder 22 facing the large diameter portion 21ab of the inner cylinder 21, the outflow portion 5 projecting to the outer circumferential side and having a cylindrical hollow portion thereinside is integrally formed with the outer cylinder 22. An opening portion of the hollow portion of the inflow portion 4 serves as an inflow port 4a, and communicates with a section formed by a gap formed between the small diameter portion 21aa of the inner cylinder 21 and the outer cylinder 22. The section formed between the small diameter portion 21aa and the outer cylinder 22 forms a first chamber (inflow-side region: front chamber) 26 serving as a rectification chamber on an inflow side through which the object before ultraviolet irradiation passes.

An opening portion of the hollow portion of the outflow portion 5 serves as an outflow port 5a, and communicates with a section formed by a gap formed between the large diameter portion 21ab of the inner cylinder 21 and the outer cylinder 22. The section formed between the large diameter portion 21ab and the outer cylinder 22 forms a third chamber (outflow-side region) 28 serving as a rectification chamber on an outflow side through which the object after the ultraviolet irradiation passes. Providing the third chamber 28 can prevent the occurrence of fluid pooling, which allows for uniform outflow of the object.

Preferably, the inflow and outflow portions 4 and 5 are formed so that the direction in which the object flows through each hollow portion is orthogonal to the longitudinal direction of the outer cylinder 22.

Additionally, the inflow portion 4 is preferably arranged at a position where there is no communication hole 65 described later on an extension of the inflow portion 4. Specifically, the inflow portion 4 is preferably arranged so that the object flowed in from the inflow portion 4 flows into the first chamber 26 formed in the small diameter portion 21aa and then passes through the communication hole 65. In this way, by allowing the object to flow into the first chamber 26 and then pass through the communication hole 65 instead of allowing the inflowed object to directly pass through the communication hole 65, nonuniformity in flow velocity distribution can be made less likely to occur.

Note that the present invention is not limited to the configuration where the object in the treatment flow path 21d is discharged from the outflow portion 5 through the third chamber 28 to an outside of the ultraviolet irradiation device 1, as illustrated in FIG. 2. For example, the outflow portion 5 may be directly provided on the outer circumferential surface of the inner cylinder 21, and the object in the treatment flow path 21d may be directly discharged to the outside of the ultraviolet irradiation device 1 without passing through the third chamber 28.

The plate 23 is preferably made of a material durable against the object, such as PTFE or steel special use stainless (SUS), and is preferably made of PTFE that has high reflectivity to ultraviolet light.

Figure 3:
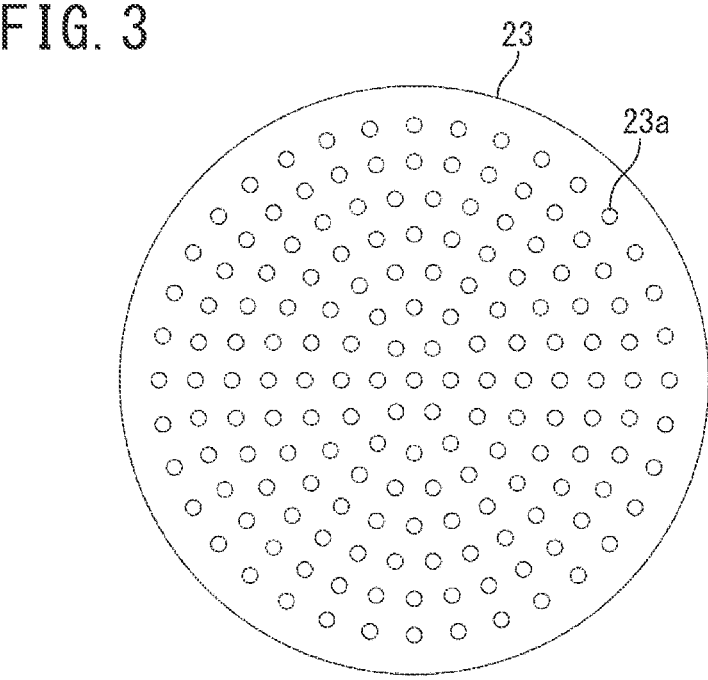
FIG. 3 is a plan view of a plate.

As illustrated in a plan view of FIG. 3, the plate 23 includes a plurality of communication holes 23a communicating between front and back surfaces thereof. In other words, the plate 23 forms a communication portion (second communication portion) including the plurality of communication holes 23a.

An opening ratio of the plate 23, i.e., a total area per plate 23 of the plurality of communication holes 23a formed in the plate 23 with respect to a cross section in a direction perpendicular to the flow in the treatment flow path 21d is preferably from 0.05 to 0.8, more preferably from 0.05 to 0.6, and still more preferably from 0.05 to 0.35. Setting the opening ratio to a value in the range of from 0.05 to 0.8 can improve the rectification effect when the object flows into the treatment flow path 21d while maintaining the strength and accuracy of the plate 23 without increasing the pressure loss.

From the viewpoint of the rectification effect, the communication holes 23a are preferably arranged concentrically at equal intervals. This arrangement can increase a symmetry of the flow of fluid between a center region and an outer circumferential region in the treatment flow path 21d.

Additionally, as the distribution of the communication holes 23a, the plate 23 is preferably arranged with the communication holes 23a not only in the vicinity of a center part of the plate 23 but also on an outside of a concentric circle having a diameter 0.85 times the inner diameter of the treatment flow path 21d. In addition, radially inner ends of the communication holes 23a arranged at the outermost circumference of the plate 23 are preferably located at a position less than the inner diameter of the treatment flow path 21d, more preferably at a position closer to the center part than a position 0.95 times the inner diameter of the treatment flow path 21d, and most preferably at a position closer to the center part than a position equal to or less than 0.90 times the inner diameter thereof. This arrangement can suppress a sudden decrease in the flow velocity of the object or the occurrence of unnecessary retention of the object on the outermost circumferential side in the treatment flow path 21d.

Returning to FIG. 2, the light emission unit 3 includes a window portion 31, a window portion support 32, and an element portion 33.

The window portion 31 is, for example, formed by a SUS plate or the like, and is formed into a circular annual shape having the same outer diameter as the outer diameter of the flange portion 22a of the outer cylinder 22. On the inner circumferential surface of the window portion 31, a first stepped portion 31a and a second stepped portion 31b having a larger inner diameter than that of the first stepped portion 31a are formed in order from a side facing the sterilization treatment unit 2, and a disk-shaped window 31c for introducing ultraviolet light, which is made of, for example, a material having a high ultraviolet transmittance, is fitted into the second stepped portion 31b. In this case, the window 31c is fitted so that surfaces of the window 31c and the window portion 31 on the element portion 33 side are flush with each other. Examples of the material having a high ultraviolet transmittance include synthetic quartz, quartz glass, crystal, and sapphire. Additionally, even resin materials would be applicable as long as they have a sufficiently high ultraviolet transmittance.

The window portion support 32 is made of, for example, SUS or the like, and formed into a circular annular shape having the same outer diameter as the outer diameter of the window portion 31. The inner diameter of the window portion support 32 is smaller than the inner diameter of the first stepped portion 31a, and is formed into a shape capable of accommodating a substrate 33b described later in an opening portion of the window portion support 32.

The element portion 33 is made of, for example, SUS or the like, and includes a disk-shaped light source support 33a having an outer diameter smaller than the outer diameter of the window portion support 32 and the substrate 33b. The substrate 33b is mounted with a light emitting element 33c such as a UVC-LED (deep ultraviolet LED) and a control circuit (not illustrated) for driving the light emitting element 33c. The control circuit communicates with an external host device, for example, via wireless communication or the like, and drives and controls the light emitting element 33c according to a command from the host device. The light emitting element 33c is preferably an element that emits ultraviolet light with a central emission wavelength of from 230 nm to 300 nm. When the light emitting element 33c would be an element emitting ultraviolet light with a central emission wavelength of from 230 nm to 300 nm, improved sterilization effect can be provided when using the ultraviolet irradiation device 1 as a sterilizer.

The substrate 33b is arranged so that a light emitting surface of the light emitting element 33c faces the window 31c. The substrate 33b is fixed by being screwed to the light source support 33a. Additionally, the light emitting element 33c is arranged so that an optical axis of irradiation light from the light emitting element 33c coincides with a longitudinal center axis of the treatment flow path 21d. When a plurality of light emitting elements 33c are arranged, the arrangement thereof has a high degree of symmetry with respect to the center axis. In the light emitting element 33c, the light emitting surface of the light emitting element 33c is preferably arranged as close as possible to the window 31c. Arranging them in close proximity to each other in this way can improve ultraviolet irradiation efficiency. Note that, as illustrated in FIG. 2, the light emitting element 33c may be provided to face an end face of the inner cylinder 21 on the outflow portion 5 side, or may be provided to face an end face of the inner cylinder 21 on the inflow portion 4 side. In other words, providing the light emitting element 33c to face at least one of the end faces will suffice.

The window portion 31, the window portion support 32, and the element portion 33 are integrally fixed by being screwed with a through bolt 34 from the element portion 33 side. In this case, by arranging and fixing an O-ring 31d made of an elastic member such as rubber onto the first stepped portion 31a, the O-ring 31d sandwiched between the first stepped portion 31a and the window 31c is deformed and brought into close contact with the first stepped portion 31a and the window 31c, thereby preventing the object from leaking out to the light emitting element 33c side from a contact portion between the window portion 31 and the window 31c.

The sterilization treatment unit 2 and the light emission unit 3 are integrally fixed at the flange portion 22a of the outer cylinder 22 by fixing the flange portion 22a, the window portion 31, and the window portion support 32 with a through bolt 38 from the window portion support 32 side. In this case, the stepped portion 22b is provided with an O-ring 22f made of an elastic member such as rubber, which prevents the object from leaking outside from a contact portion between the window portion 31 and the outer cylinder 22. Additionally, a flat ring packing 22g is provided between an end portion of the inner cylinder 21 on the communication port 21a side and the window portion 31. The flat ring packing 22g acts as a cushioning material when the inner cylinder 21 is pressed against the window portion 31 by the lid unit 6. In addition, elasticity of the flat ring packing 22g allows the inner cylinder 21 to be in a constant relative position with respect to the outer cylinder 22. An elastomer such as PTFE, a silicon resin elastomer, or a fluororesin elastomer is preferably applied as the flat ring packing 22g.

Figure 4:
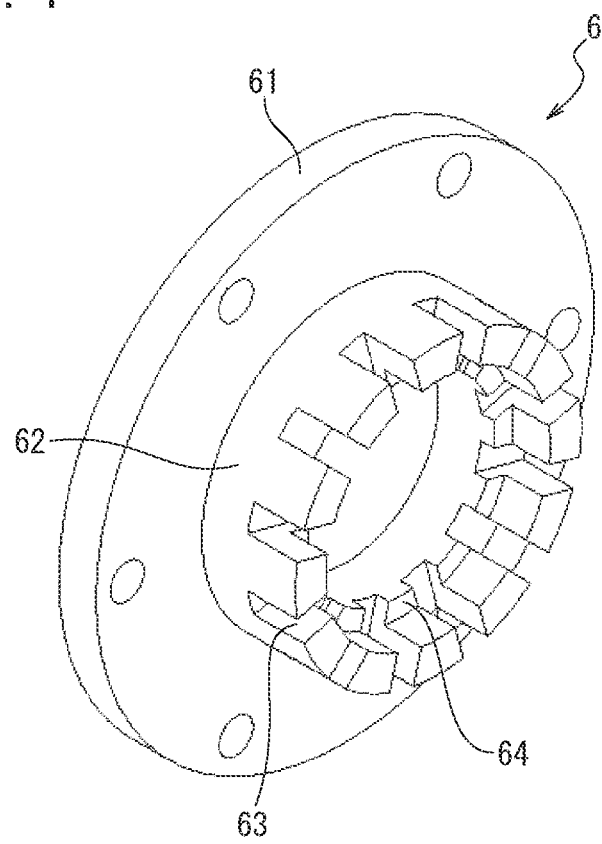
FIG. 4 is a perspective view of a lid unit.

The lid unit 6 is provided to close the opening portion of the inner cylinder 21. FIG. 4 is a perspective view of the lid unit 6, FIG. 5A is a top view of the lid unit 6, and FIG. 5B is a cross-sectional view taken along line A-A' of FIG. 5A.

The lid unit 6 is made of, for example, SUS or the like, and, as illustrated in FIG. 4, includes a disk portion 61 and a circular annular portion 62 formed on one surface of the disk portion 61. The disk portion 61 and the circular annular portion 62 are integrally formed.

The disk portion 61 has the same diameter as the outer diameter of the flange portion 22c of the outer cylinder 22.

The circular annular portion 62 is formed so that an axial center thereof coincides with a circular center of the disk portion 61. At an end portion of the circular annular portion 62 are formed a plurality of slits 63 having the same shape at equal intervals in a circumferential direction. Additionally, a stepped portion 64 is formed inside the end portion of the circular annular portion 62, and the slits 63 are formed to reach a position between the stepped portion 64 and a surface of the disk portion 61 from the end portion of the circular annular portion 62. In FIG. 4, twelve slits 63 are formed.

Here, as illustrated in FIG. 5B, when, in the circular annular portion 62, a circular annular part having a higher height is defined as a protrusion (first protrusion) 62out and a circular annular part having a lower height is defined as a protrusion (second protrusion) 62in, the protrusion 62in has an outer diameter same as an inner diameter of the protrusion 62out, and has an inner diameter same as the inner diameter of the inner cylinder 21. The protrusion 62out has an outer diameter substantially same as the inner diameter of the outer cylinder 22, and has an inner diameter substantially same as the outer diameter of the inner cylinder 21. It is preferable that the outer and inner diameters of the protrusion 62out allow for fitting of a tip of the protrusion 62out into the gap between the inner cylinder 21 and the outer cylinder 22, and a gap between the protrusion 62out and the inner cylinder 21 and a gap between the protrusion 62out and the outer cylinder 22 are small.

Therefore, when the lid unit 6 is fitted into the inner cylinder 21 so as to close the opening portion of the inner cylinder 21, the outer diameter of the disk portion 61 of the lid unit 6 coincides with the outer diameter of the flange portion 22c, and the tip of the protrusion 62out fits into the gap between the inner and outer cylinders 21 and 22, i.e., into the first chamber 26 to limit movement of the lid unit 6 in a direction orthogonal to the longitudinal direction of the treatment flow path 21d. Additionally, the end face of the inner cylinder 21 and an end face of the protrusion 62in come into contact with each other, and the disk portion 61 of the lid unit 6 and the flange portion 22c come into contact with each other, thereby limiting movement of the lid unit 6 to the sterilization treatment unit 2 side. The height of the protrusion 62out is set to a height where the end portion of the protrusion 62out reaches a position closer to the light emission unit 3 than the plate 23 when the lid unit 6 is fixed to the sterilization treatment unit 2.

The lid unit 6 and the sterilization treatment unit 2 are integrally fixed by being screwed with a through bolt 68 at a portion where the disk portion 61 of the lid unit 6 and the flange portion 22c overlap. In this case, the stepped portion 22d of the outer cylinder 22 is provided with an O-ring 69 made of an elastic member such as rubber, thereby preventing the object from leaking outside from a contact portion between the lid unit 6 and the outer cylinder 22.

Here, as illustrated in FIG. 4, the lid unit 6 is formed with the slits 63. The slits 63 are formed up to a position closer to the disk portion 61 side than the stepped portion 64. Therefore, by fixing the lid unit 6 to the sterilization treatment unit 2, portions of the slits 63 closer to tips thereof are closed by the inner cylinder 21, whereas portions of the slits 63 closer to the disk portion have a part not closed by the inner cylinder 21. As a result, as illustrated in FIG. 2, the lid unit 6 and the inner cylinder 21 form the same number of communication holes 65 oriented in the radial direction as the number of the slits 63, which are defined by the slits 63 and the inner cylinder 21. In other words, the lid unit 6 and the inner cylinder 21 form a communication portion R1 as a first communication portion including twelve communication holes 65. Furthermore, a columnar space is formed between an inside of the circular annular portion 62 of the lid unit 6, the plate 23, and a region of the inner cylinder 21 on the lid unit 6 side. The space is a second chamber (retention portion: front chamber) 27 that serves as an inflow-side rectification chamber. Providing the second chamber 27 can prevent flow velocity fluctuations in the treatment flow path 21d when the flow rate of the object fluctuates, thereby enabling improved rectification effect. Providing the second chamber 27 can also reduce inter-individual variability due to assembly accuracy.

Here, a "flow path pressure loss coefficient average value/number of flow paths" in the communication portion R1 is preferably from 0.5 to 30 times, more preferably from 0.5 to 5.0 times, and still more preferably from 0.5 to 2.0 times an "average diameter/(4th power of longitudinal cross section equivalent inner diameter)" of the first chamber 26. By setting the "flow path pressure loss coefficient average value/number of flow paths" in the communication portion R1 to a value within such a range, a sufficient rectification effect can be obtained without increasing the pressure loss.

Note that the flow path pressure loss coefficient as used herein refers to a coefficient represented by the following formula (1) in each flow path of a plurality of communication holes 65:

$$\text{Flow path pressure loss coefficient} = \{(\text{flow path length})/(\text{square of flow path equivalent inner diameter})\}/\text{flow path cross-sectional area} \quad (1)$$

Figure 6:
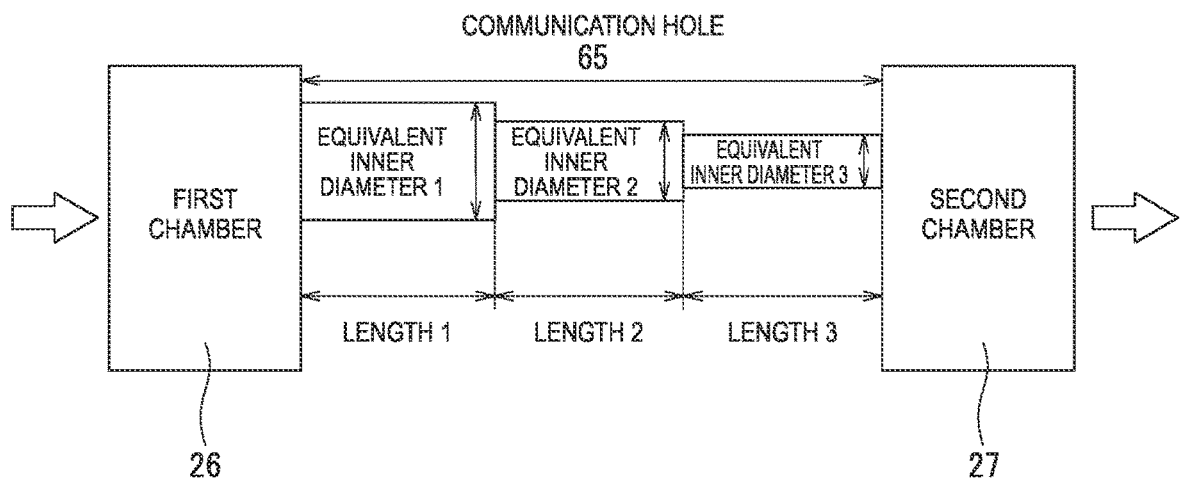
FIG. 6 is an illustrative view of a method for calculating a fluid pressure loss coefficient.

Note that, as illustrated in FIG. 6, when the cross-sectional area of a flow path of the communication hole 65 changes, the flow path pressure loss coefficient is calculated according to the following formula (2). Additionally, n in formula (2) represents the number of different cross-sectional areas in the flow path. In the case of FIG. 6, n=3.

$$\text{Flow path pressure loss coefficient} = [\{(\text{flow path length 1})/(\text{square of flow path equivalent inner diameter})\}/\text{flow path cross-sectional area 1}] + [\{(\text{flow path length 2})/(\text{square of flow path equivalent inner diameter})\}/\text{flow path cross-sectional area 2}] + \ldots + [\{(\text{flow path length } n)/(\text{square of flow path equivalent inner diameter})\}/\text{flow path cross-sectional area } n] \quad (2)$$

The "flow path equivalent inner diameter" as used in formulae (1) and (2) refers to "4 times the communication path cross-sectional area/communication path cross-sectional circumference" in the communication hole 65, i.e., "4 times the cross-sectional area of communication hole 65)/(cross-sectional circumference of communication hole 65)."

The number of flow paths represents the number of communication holes 65.

The average diameter of the first chamber 26 represents an average value of the inner and outer diameters in an annular flow path being the first chamber 26.

The longitudinal cross section of the first chamber 26 represents a flow path cross section of the first chamber 26 in a cross section in a direction parallel to the longitudinal direction of the treatment flow path 21d including a center axis of the ultraviolet irradiation device 1 as illustrated in FIG. 2. Note that when the expression "flow path cross section" is simply used, it represents a flow path cross section in a direction perpendicular to a flow direction in the flow path.

Depending on the device structure, such as the size and shape of the ultraviolet irradiation device 1, the flow path cross sectional area of the same communication hole 65 may change in the middle of the flow path. However, designing the communication portion R1 according to the above formula (2) will suffice. This can improve rectification effect, and also can improve flexibility in the device structure.

In addition, the communication holes 65 are preferably arranged on a side wall of the second chamber 27, and a total area ratio of a total opening area of the communication holes 65 at a contact portion between the second chamber 27 and the communication hole 65 to a total area of the side wall is preferably from 0.03 to 0.8. Setting the ratio within the range can prevent the pressure loss from being too much, and can maintain strength and accuracy of the communication holes 65. Note that the total area of the side wall as used herein refers to the area of the side wall including the circular annular portion 62 and the inner cylinder 21 arranged with the annular member 21ca between the disk portion 61 and the plate 23 in FIG. 2.

In the ultraviolet irradiation device 1 having the above configuration, the object flowing into the inflow port 4a is introduced into the first chamber 26 through the inflow portion 4, moves through the first chamber 26 along the longitudinal direction of the treatment flow path 21d, and is introduced into the second chamber 27 from a direction intersecting with the longitudinal direction of the treatment flow path 21d through the plurality of communication holes 65 forming the communication portion R1 formed by the lid unit 6 and the sterilization treatment unit 2. Then, the object introduced into the second chamber 27 is introduced into the treatment flow path 21d from the longitudinal direction of the treatment flow path 21d through the plate 23 including the plurality of communication holes 23a. The object, when passing through the treatment flow path 21d, is sterilized by ultraviolet irradiation using the light emitting element 33c, then discharged from the treatment flow path 21d through the communication ports 21a to the third chamber 28 from the direction intersecting the longitudinal direction of the treatment flow path 21d, and discharged to the outside of the ultraviolet irradiation device 1 from the outflow port 5a through the outflow portion 5.

Effects

In the ultraviolet irradiation device 1 according to the embodiment of the present invention, the object is allowed to flow into the treatment flow path 21d through the first and second chambers 26 and 27 before reaching the treatment flow path 21d from the inflow portion 4. The object input to the inflow portion 4 is adjusted to have a more uniform flow velocity by passing through the first and second chambers 26 and 27, respectively, and then, is introduced into the treatment flow path 21d. Therefore, providing the first and second chambers 26 and 27 can further improve the rectification effect, as a result of which the object to be introduced into the treatment flow path 21d can be adjusted to flow more uniformly.

Additionally, the communication portion R1 communicating between the first chamber 26 and the second chamber 27 has the structure in which the communication holes 65 are defined by the slits 63 and the inner cylinder 21. Specifically, the slits 63 are formed in the lid unit 6, then the lid unit 6 and the inner cylinder 21 are assembled together to define the communication holes 65, which results in formation of the communication portion R1 including the plurality of communication holes 65 due to the formation of the plurality of slits 63. The slits 63 can be formed with relatively high accuracy, and the lid unit 6 and the inner cylinder 21 can be assembled with relatively high accuracy. Accordingly, inter-individual variability of the communication holes 65 due to assembly errors can be reduced, so that variability in the rectification effect due to assembly errors can be reduced. Thus, the reduced influence of assembly errors and the like enables realization of the ultraviolet irradiation device 1 having excellent robustness. This can prevent a gap causing an unintended flow from being created in the flow path in the ultraviolet irradiation device 1, and can prevent a flow path imbalance (so-called one-sided flow) from occurring due to insufficient accuracy of flow path dimensions.

In addition, by providing the communication portion R1 and the plate 23 on the inflow side, rectification is performed not only by the communication portion R1 but also by the plate 23. Therefore, the object can be rectified more accurately than a case where the object is allowed to pass through only the communication portion R1 or only the plate 23. As a result, it is possible to suppress the occurrence of a fast flowing region in the treatment flow path 21$d$ due to flow rate fluctuations, which can further ensure the uniformity of the flow of the object in the treatment flow path 21$d$. Therefore, the occurrence of an insufficiently irradiated region due to flow rate fluctuations can be further avoided. In addition, providing the communication portion R1 and the plate 23 allows for more accurate adjustment of the flow velocity distribution in the treatment flow path 21$d$, so that the flow of the object in the treatment flow path 21$d$ can be made closer to a target flow. Thus, favorable sterilization performance can be exhibited while further suppressing the pressure loss in the entire ultraviolet irradiation device 1.

Figure 7:
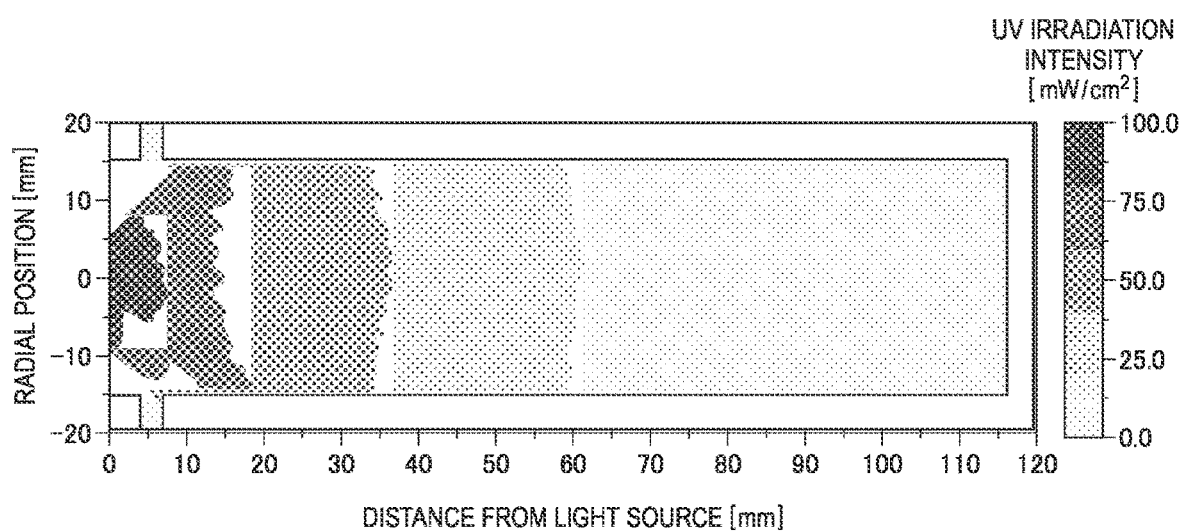
FIG. 7 is one example of the distribution of illuminance in a treatment flow path.

When the flow velocity of the object matches illuminance distribution in the treatment flow path 21$d$, there occurs no high flow velocity region with respect to the illuminance, so that a sufficient sterilization effect tends to be easily obtained. As illustrated in FIG. 7, in the illuminance distribution in the treatment flow path 21$d$, when the illuminance in the flow path cross section is substantially uniform in an area of the treatment flow path 21$d$ other than a vicinity of the light source (light emitting element 33$c$), a wall flow velocity of the object in the treatment flow path 21$d$ is always 0. Thus, substantially ensuring the uniformity of the flow of the object in the treatment flow path 21$d$ can be expected to improve sterilization ability.

In addition, by providing the plurality of communication portions including the plurality of communication holes, such as the communication portion R1 and the plate 23, the design width of arrangement of the communication holes in one communication portion is widened compared with a case where one communication portion is provided, as well as combining the plurality of communication portions can realize more velocity flows. Therefore, the flow velocity distribution of the object in the treatment flow path can be adjusted to a more appropriate flow velocity distribution.

The ultraviolet irradiation device 1 according to the embodiment of the present invention also specifies the arrangement position and opening ratio of the communication holes 23$a$ in the plate 23. Therefore, the rectification effect can be improved, and the uniformity of the flow of the object in the treatment flow path 21$d$ can be ensured.

The ultraviolet irradiation device 1 according to the embodiment is also provided with the first chamber 26 formed by the annular flow path on the outer circumference of the treatment flow path 21$d$. This can further improve the rectification effect as compared with a case where the first chamber 26 is not provided.

Additionally, the lid unit 6 is configured so that the tip of the protrusion 62out is fitted into the gap between the inner cylinder 21 and the outer cylinder 22, thereby limiting the movement of the lid unit 6 in the direction orthogonal to the longitudinal direction of the inner cylinder 21. In other words, the protrusion 62out defines the distance between the inner and outer cylinders 21 and 22. Then, the O-ring 24 is provided at a substantially center part of the longitudinal direction between the inner and outer cylinders 21 and 22.

The O-ring 24 is in close contact with the inner and outer cylinders 21 and 22, and divides the above gap into the first chamber 26 and the third chamber 28. Therefore, the O-ring 24 and the protrusion 62out define the position of the inner cylinder 21 relative to the outer cylinder 22. Accordingly, without complicated adjustments, the inner cylinder 21 can be held in an appropriate position inside the outer cylinder 22. In addition, even when vibration is applied by the object or the like, misalignment or the like of the inner cylinder 21 inside the outer cylinder 22 is unlikely to occur since the inner cylinder 21 is positioned by the lid unit 6 and the O-ring 24. Thus, the inner cylinder 21 can be maintained at the appropriate position. If the inner cylinder 21 is misaligned inside the outer cylinder 22, the flow of the object in the treatment flow path 21$d$ becomes nonuniform, which results in nonuniform ultraviolet irradiation. Accordingly, preventing the misalignment of the inner cylinder 21 allows for more accurate ultraviolet irradiation.

In addition, the protrusion 62in is provided inside the protrusion 62out to form the second chamber 27 surrounded by the circular annular portion 62, the inner cylinder 21, and the plate 23, thereby preventing a stepped portion from being formed on a side surface of the second chamber 27. Therefore, retention of the object in the second chamber 27 due to the formation of a stepped portion or the like can be made unlikely to occur. Furthermore, as described above, the misalignment of the inner cylinder 21 in the outer cylinder 22 can be prevented by the lid unit 6 and the O-ring 24, so that the shape of the second chamber 27 can be stably maintained even when vibration is applied by the object or the like. This can prevent the rectification effect from being reduced due to a change in the shape of the second chamber 27 caused by an external disturbance.

Additionally, the structure for positioning the inner cylinder 21 is provided as the circular annular portion 62 in the lid unit 6, and the slits 63 for defining the communication holes 65 are also provided in the lid unit 6. Therefore, high processability can be achieved without compromising productivity. In other words, if the inner cylinder 21 is to have the structure equivalent to the circular annular portion 62 and the slits 63, it is necessary to use a material having high ultraviolet resistance for the inner cylinder 21, which narrows down the range of material choices, and such a material tends to be inferior in processability. Moreover, even if the outer cylinder 22 is to have the structure equivalent to the circular annular portion 62 and the slits 63, the processability is inferior. In other words, the structure equivalent to the circular annular portion 62 and the slits 63 is generally manufactured by injection molding a thermoplastic resin, which requires use of many molds having complicated structures. On the contrary, when the lid unit 6 is designed to have the structure equivalent to the circular annular portion 62 and the slits 63, the structure can be manufactured by fewer molds that have simpler structures than in the case where the outer cylinder 22 is to have the structure.

EXAMPLES

Examples of the ultraviolet irradiation device 1 according to the present invention will be described below.

Example 1

Figure 8:
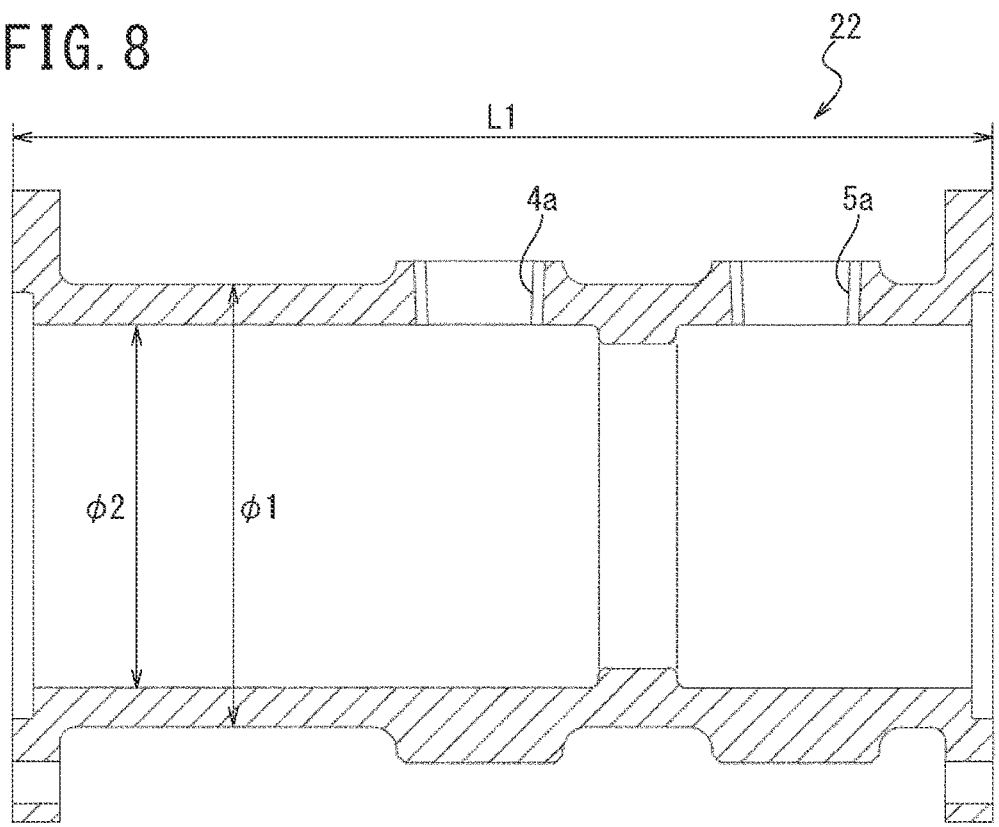
FIG. 8 is a diagram illustrating the inner diameter, outer diameter, and length of an outer cylinder.

As illustrated in FIG. 8, in the ultraviolet irradiation device 1 of Example 1, the outer cylinder 22 had an outer diameter $\phi 1$ of $\phi 56$ mm, an inner diameter $\phi 2$ of $\phi 46$ mm, and a length L1 of 124 mm, and was made of resin.

Additionally, the inflow port 4a and the outflow port 5a, respectively, had a diameter of ϕ7.5 mm. As the inner cylinder 21, a PTFE tube having an outer diameter (small diameter portion 21aa) of ϕ40 mm, an inner diameter of ϕ30 mm, and a length of 115 mm was used. There were provided twelve slits 63, whereby twelve communication holes 65 were formed between the inner cylinder 21 and the lid unit 6. The communication holes 65 were 4 mm in width and 2 mm in height. In addition, as the plate 23, a plate having an outer diameter of ϕ32 mm and a thickness of 1.5 mm and formed with 85 concentric communication holes 23a having a diameter of 1.4 mm was used. The diameter of a circle connecting inner ends of the plurality of communication holes 23a arranged at an outermost circumference of the plate 23 was ϕ28 mm, and the ratio of the diameter to the diameter of the treatment flow path 21d was set to 0.93. The installation position of the plate 23 was set to 4 mm inside the end face of the inner cylinder 21 on the lid unit 6 side so that when the object flowed into the treatment flow path 21d, it did not pass through the inside of the treatment flow path 21d without passing through the plate 23. In order to fix the plate 23, the stepped portion 21c having a depth of 5.5 mm and a radial distance of 1 mm was formed inside the inner cylinder 21 on the lid unit 6 side. Additionally, as the annular member 21ca for fixing the plate 23, a member having an outer diameter of ϕ32 mm, an inner diameter of 30 mm, and a height of 4 mm was used. Furthermore, the window 31c made of synthetic quartz having a diameter of ϕ32 mm and a thickness of 3 mm was installed inside the window portion 31 made of SUS having a diameter of ϕ68 mm and a thickness of 7 mm. As the flat ring packing 22g, a thin packing made of PTFE was used. As the communication ports 21a of the inner cylinder 21, through holes having a diameter of ϕ2.5 mm were provided at 1 mm inward from the end face of the inner cylinder 21. A plate made of Al was used as the element portion 33, and inside the plate made of Al was provided the substrate 33b mounted with the light emitting element 33c. The diameter of the lid unit 6 was ϕ68 mm, which was larger than the outer diameter ϕ1 of the outer cylinder 22. In addition, the diameter of the flange portion of the outer cylinder 22 was also set to ϕ68 mm to match the diameter of the disk portion 61.

Evaluation of Example 1

Figure 9:
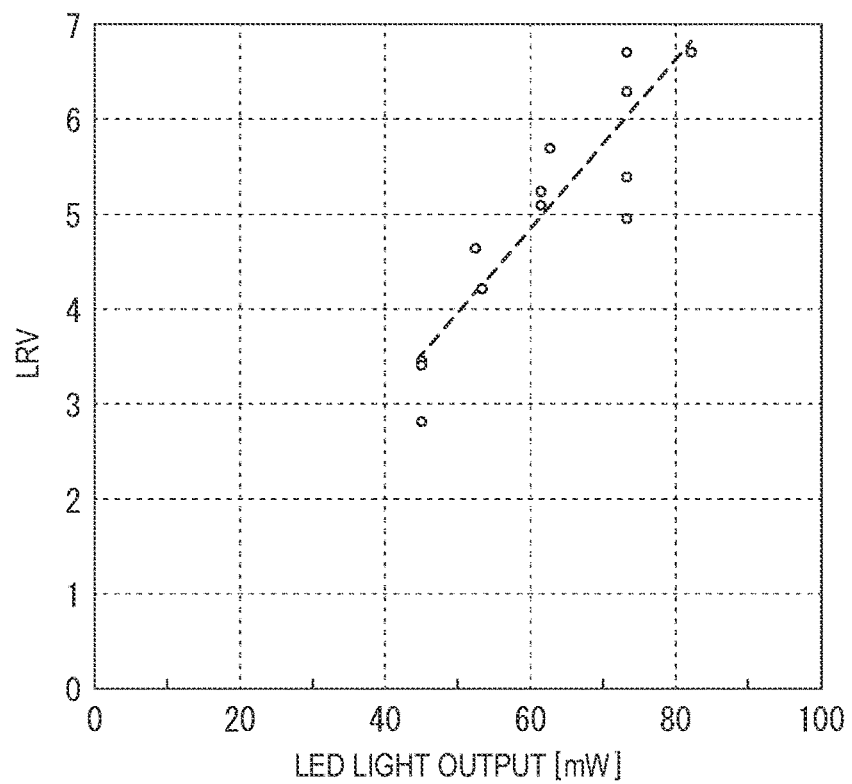
FIG. 9 is a graph illustrating results of sterilization ability measurement.

Using the ultraviolet irradiation device 1 having the above configuration as a fluid sterilization module, the sterilization performance thereof was evaluated by measuring the sterilization ability for water containing *Escherichia coli*. FIG. 9 illustrates results of the sterilization ability measurement. In FIG. 9, the horizontal axis represents light output [mW] of an LED having a peak wavelength of 265 [nm], and the vertical axis represents sterilization performance LRV when the water containing *Escherichia coli* (Eq. Power, bacterial strain: *E. Coli*) was allowed to pass through the treatment flow path 21d at a flow rate of 5 L/min. As illustrated in FIG. 9, when the light output [mW] of the LED having a peak wavelength of 265 [nm] was 40 mW or more, the LRV was 3 or more, which confirms that 99.9% sterilization can be achieved.

Example 2

Using the ultraviolet irradiation device 1 illustrated in FIG. 1, the uniformity of flow in the treatment flow path 21d was measured. The uniformity of the flow was evaluated by the parameter of surface uniformity. When the illuminance in the cross section in the treatment flow path 21d is substantially uniform as described above, the more uniform the flow velocity in the treatment flow path 21d, the more improved the sterilization ability can be expected. Thus, the higher the surface uniformity, the higher the sterilization ability.

The surface uniformity is expressed by the following formula (3). As the surface uniformity obtained by formula (3) is closer to "1", it indicates a higher flow uniformity. Note that, in formula (3), Σf represents the sum of discrete regions on a certain surface. In addition, the area average value refers to an average value of target scalar values on the certain surface.

$$\text{Surface uniformity} = 1 - \frac{\sum_f |\phi_f - \bar{\phi}| A_f}{2|\bar{\phi}|\sum_f A_f}$$

ϕ: flow velocity $\bar{\phi}$: area average value of ϕ

$\phi_f$: flow velocity value on certain surface $A_f$: area of certain surface

Note that the "certain surface" described in $\phi_f$ and $A_f$ refers to a flow path cross section to be targeted.

Evaluation 1 of Example 2

Figure 10:
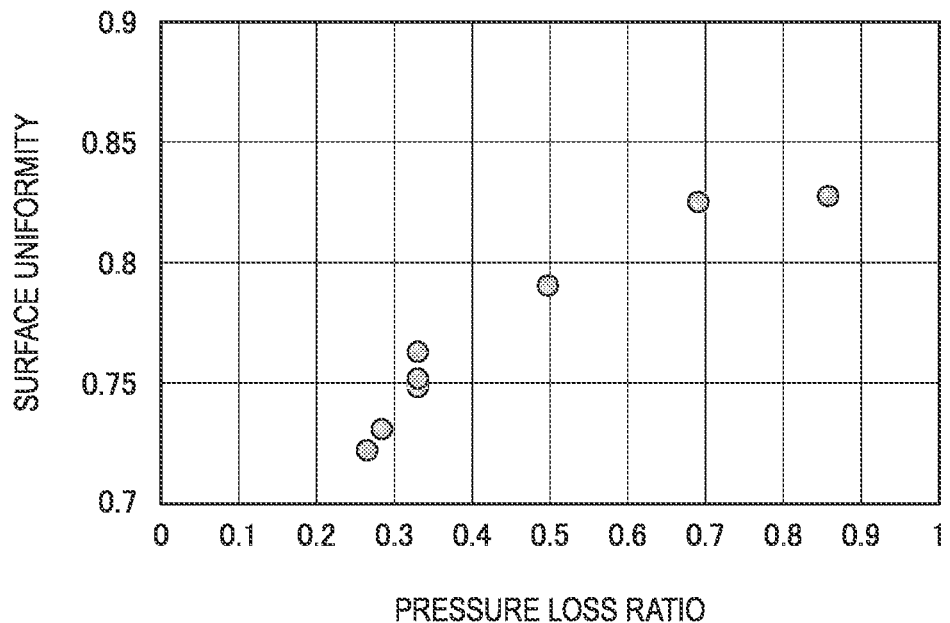
FIG. 10 is a diagram illustrating a correspondence between pressure loss ratio and surface uniformity.

FIG. 10 illustrates a correspondence between surface uniformity and pressure loss ratio when the dimensions of the communication portion R1, the number of the slits 63, and the longitudinal cross-sectional shape of the first chamber 26 are changed. In FIG. 10, the horizontal axis represents pressure loss ratio, and the vertical axis represents surface uniformity. Note that the pressure loss ratio represents the ratio of the "flow path pressure loss coefficient average value/number of flow paths" of the communication portion R1 to the "average diameter/(4th power of longitudinal cross section equivalent inner diameter)" of the first chamber 26. As illustrated in FIG. 10, when the pressure loss ratio is 0.5 or more, the surface uniformity is substantially 0.8 or more, indicating that the uniformity of the flow of the object in the treatment flow path 21d is relatively high.

Evaluation 2 of Example 2

Figure 11:
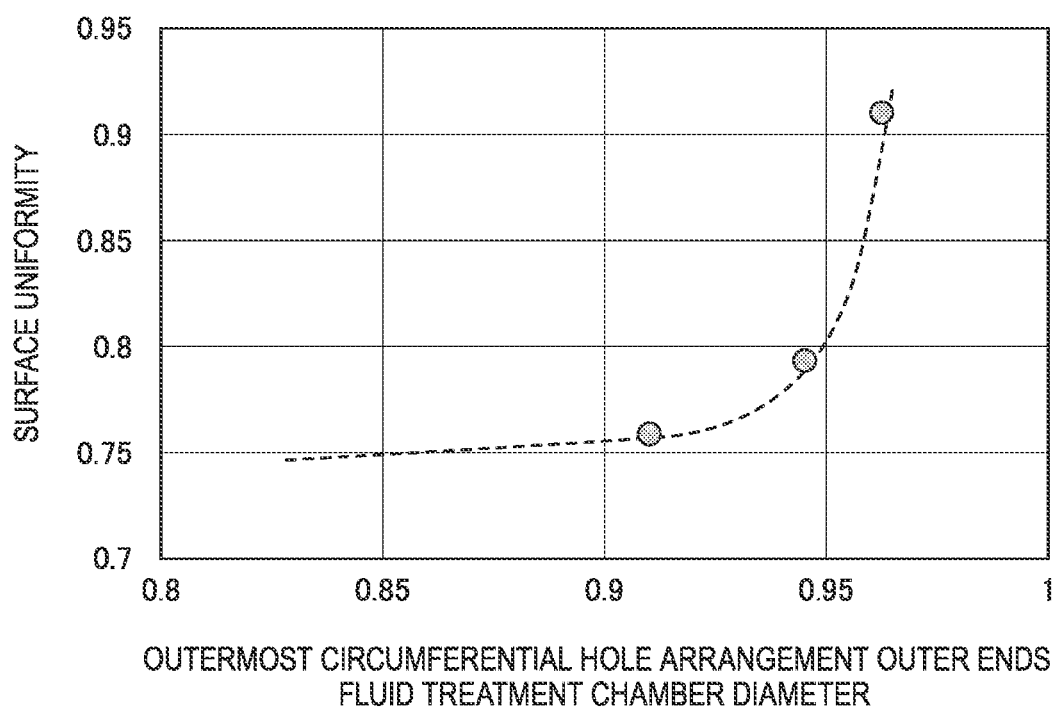
FIG. 11 is a diagram illustrating a correspondence between a ratio of outermost circumferential hole arrangement outer ends to a fluid treatment chamber diameter and surface uniformity.

Next, using the ultraviolet irradiation device 1 having the above configuration, the ratio of the outermost hole arrangement diameter to the diameter of the treatment flow path 21d was changed to obtain results given in Table 1. An effective range was estimated from the results to obtain results as given in FIG. 11. It can be seen that setting the ratio to 0.9 or more can increase surface uniformity. Additionally, the test results confirmed that when extrapolation is performed, a surface uniformity of 0.75 or more can be ensured by setting the ratio to 0.85 or more. Note that, in FIG. 11, the horizontal axis represents "outermost circumferential hole arrangement outer ends/fluid treatment chamber (i.e., the second chamber 27) diameter".

TABLE 1

|  | Ratio of outermost circumferential hole arrangement diameter to treatment flow path diameter | Cylinder diameter | Hole diameter | Number of holes | Surface uniformity |
|---|---|---|---|---|---|
| CASE 1 | 0.910 | 40 | 1.1 | 163 | 0.759 |
| CASE 2 | 0.945 | 40 | 1.4 | 160 | 0.794 |
| CASE 3 | 0.963 | 40 | 1.1 | 168 | 0.911 |

Modifications (1) Although the above embodiment has described the case where the first chamber 26, the second chamber 27, and the third chamber 28 are provided, the present invention is not limited thereto.

For example, the object may be directly supplied to the first chamber 26 without providing the inflow portion 4. It also suffices to configure so that the object flows into the treatment flow path 21d through at least two chambers before flowing into the treatment flow path 21d, and it may be configured that the object flows into the treatment flow path 21d through three or more chambers in consideration of the rectification effect, fluid treatment capacity, and the like. For example, a plurality of communication portions R1 may be provided, the communication portion R1 and a plurality of plates 23 may be provided, or each of the communication portion R1 and the plate 23 may be provided in plural. It also suffices that the communication portion between the first and second chambers 26 and 27 has the plurality of communication holes.

Figure 12A:
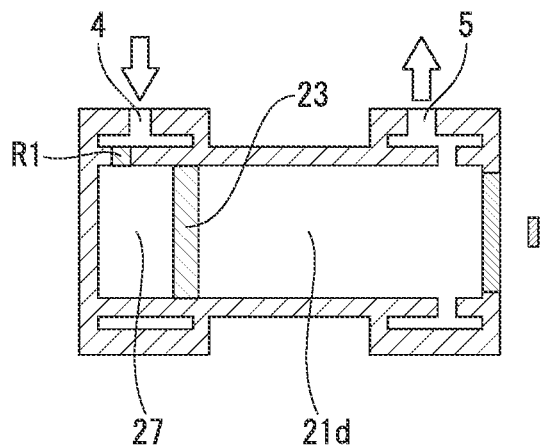
FIGS. 12A to 12D are schematic configuration diagrams illustrating modifications of the ultraviolet irradiation device according to the present invention.

Additionally, for example, as illustrated in FIG. 12A, it may be configured that the object flowing into the inflow portion 4 is directly supplied to the communication portion R1 without providing the first chamber 26, and similarly, the object output from the treatment flow path 21d may be discharged directly from the outflow portion 5 without providing the third chamber 28.

Figure 12B:
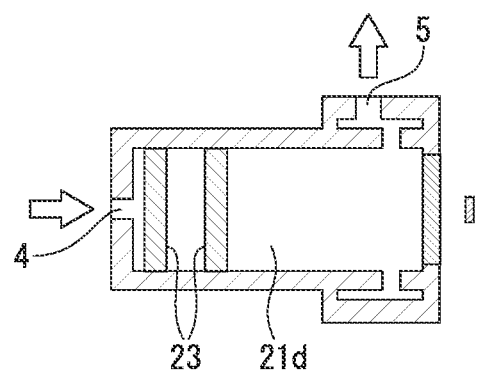
Figure 12C:
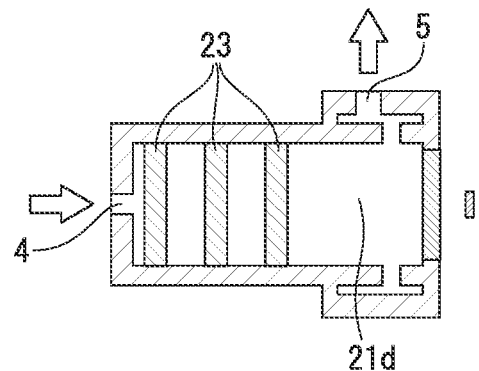
Figure 12D:
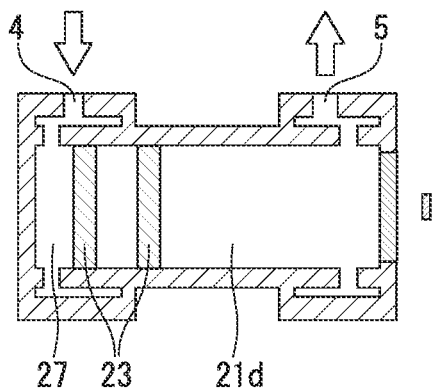

In addition, the present invention is not limited to the case where each of the communication portion R1 and the plate 23 is provided. As illustrated in FIG. 12B, the plurality of plates 23 may be provided in series without providing the communication portion R1. In this case, it may also be configured that the object passes through the plates 23 directly from the inflow portion 4 without providing the second chamber 27. Furthermore, as illustrated in FIG. 12C, three or more plates 23 may be provided in series. When only the plate 23 is provided as the communication portion, the inflow portion 4 may be provided on an extension of the treatment flow path 21d in the longitudinal direction to allow the object to flow in from the longitudinal direction of the treatment flow path 21d, as illustrated in FIGS. 12B and 12C. Alternatively, as illustrated in FIG. 12D, the inflow portion 4 may be provided to be oriented in the direction orthogonal to the longitudinal direction of the treatment flow path 21d, as in the present embodiment illustrated in FIG. 2. Still furthermore, the communication portion R1 may be provided in plural, or each of the communication portion R1 and the plate 23 may be provided in plural.

Providing the plurality of communication portions R1 or the plurality of plates 23 serving as the communication portions increases the rectification effect. However, as the number of the communication portions increases, the ultraviolet irradiation device 1 becomes larger in size, and the pressure loss may increase. It is therefore preferable to determine the number of communication portions by taking these concerns into account.

Note that FIGS. 12A to 12D illustrate schematic configurations of the ultraviolet irradiation devices.

Figure 13:
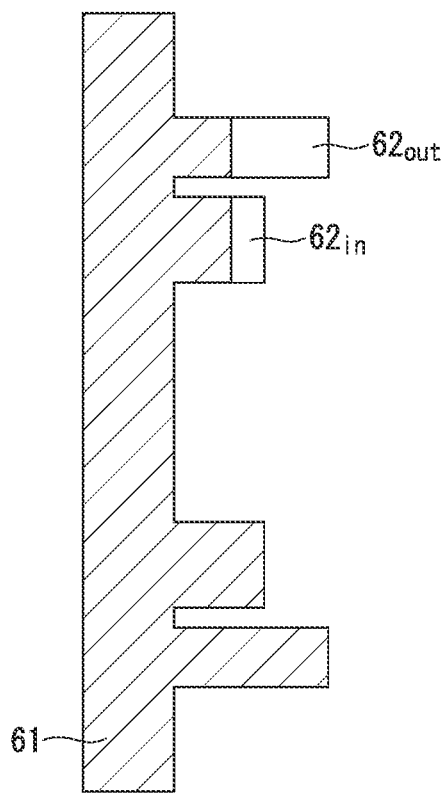
FIG. 13 is a cross-sectional view illustrating a modification of the lid unit according to the present invention.

(2) The description has been given of the case of the lid unit 6 where, in the circular annular portion 62, the protrusions 62out and 62in are connected and integrally formed, as illustrated in FIGS. 5A and 5B. However, the lid unit 6 is not limited to the above case. For example, as illustrated in FIG. 13, the present invention can be applied to even a case of the lid unit 6 where, in the circular annular portion 62, the protrusions 62out and 62in are formed apart from each other.

Figure 14:
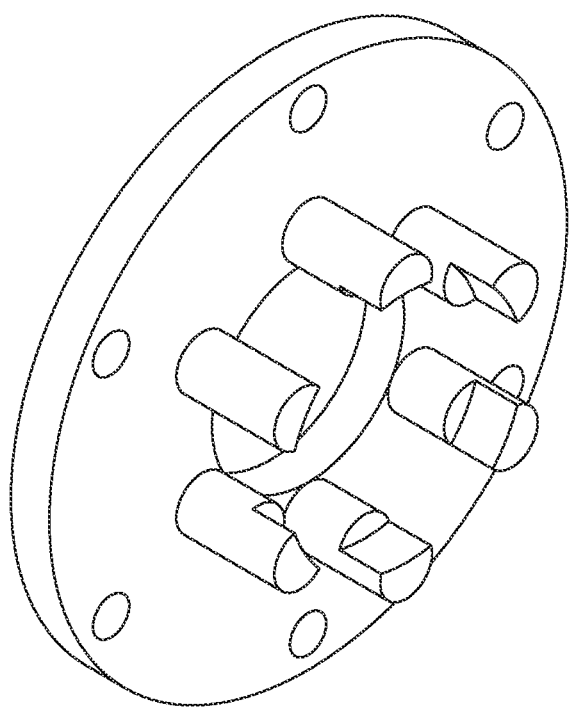
FIG. 14 is a perspective diagram illustrating a modification of the lid unit according to the present invention.

It also suffices that the functions and effects equivalent to those of the circular annular portion 62 with the protrusions 62out and 62in integrally formed can be obtained. For example, as illustrated in FIG. 14, the circular annular portion 62 may be formed by arranging cylinders on a circle, each of the cylinders including a notch for holding the inner cylinder 21 formed at tips thereof. Alternatively, not limited to a cylinder, the circular annular portion 62 may be formed by arranging columnar members having a polygonal cross-sectional shape on a circle, each of the columnar members including a notch for holding the inner cylinder 21 formed at tips thereof.

(3) In addition, the communication holes 65 do not necessarily have to be oriented in the radial direction, i.e., the direction orthogonal to the longitudinal direction of the inner cylinder 21. It suffices that the communication holes 65 are oriented in a direction intersecting with the longitudinal direction of the inner cylinder 21. The communication holes 65 do not also necessarily have to be arranged evenly, and do not have to be oriented in the same direction. The orientation and arrangement position of the communication holes 65 may be adjusted according to a desired flow velocity distribution of the object in the treatment flow path 21d.

Similarly, the communication holes 23a formed in the plate 23 do not necessarily have to be oriented in a direction orthogonal to the plate 23 main body, and all the communication holes 23a do not have to be oriented in the same direction. In addition, the plate 23 does not have to be provided to be parallel to the cross section of the treatment flow path 21d, and the plate 23 does not have to be flat or circular.

Figure 15F:
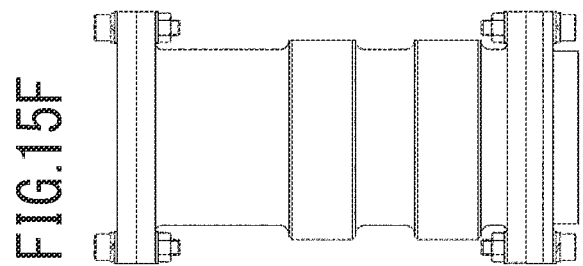
FIGS. 15A to 15F are six side views illustrating one example of the ultraviolet irradiation device according to the present invention.
Figure 15C:
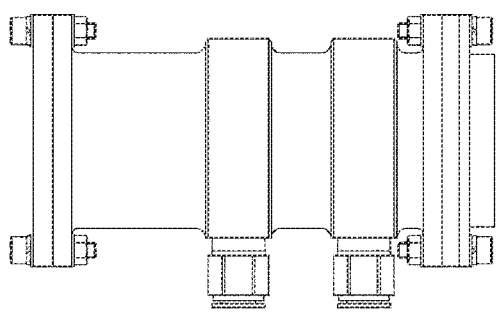
Figure 15D:
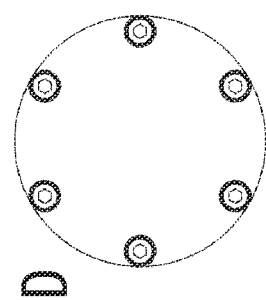
Figure 15A:
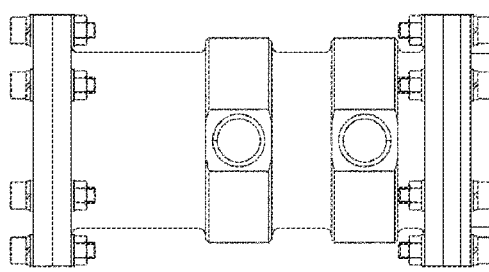
Figure 15E:
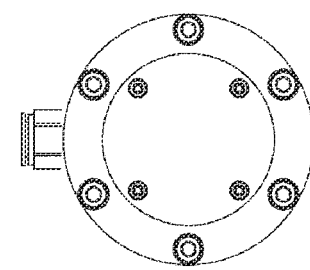
Figure 15B:
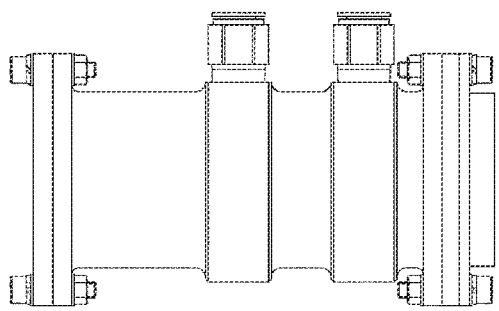

FIGS. 15A to 15F illustrate six side views of one example of the ultraviolet irradiation device 1 according to an embodiment of the present invention. FIG. 15A is a front view, FIG. 15B is a left side view, FIG. 15C is a right side view, FIG. 15D is a plan view, FIG. 15E is a bottom view, and FIG. 15F is a back view.

Note that the scope of the present invention is not limited to the illustrated and described exemplary embodiments, and includes all embodiments that provide effects equivalent to those for which the present invention is intended. Additionally, the scope of the present invention can be defined by any desired combination of specific features out of all disclosed respective features.

REFERENCE SIGNS LIST

1: Ultraviolet irradiation device
2: Sterilization treatment unit
3: Light emission unit
4: Inflow portion
5: Outflow portion
6: Lid unit 21: Inner cylinder
21d: Treatment flow path
22: Outer cylinder
23: Plate
23a: Communication hole
26: First chamber
27: Second chamber
28: Third chamber
33c: Light emitting element
62in: Protrusion
62out: Protrusion
65: Communication hole
R1: Communication portion

The invention claimed is:
1. An ultraviolet irradiation device, comprising:
a cylindrical portion configured to form a cylindrical treatment flow path extending in a longitudinal direction and have at least one open end;
an inflow portion configured to allow an object to flow into the treatment flow path from the at least one open end side of the cylindrical portion;
a light emitting element provided at least at one end of the cylindrical portion and configured to irradiate the object passing through the treatment flow path with ultraviolet light;
an outer cylinder configured to accommodate the cylindrical portion, in which a space is provided between an outer circumferential surface of the cylindrical portion and an inner circumferential surface of the outer cylinder;
a dividing member including a first portion in contact with the outer circumferential surface of the cylindrical portion and a second portion in contact with the inner circumferential surface of the outer cylinder, wherein the first portion and the second portion are made of an elastic member, wherein the dividing member divides the space into an inflow-side region through which the object before being irradiated with the ultraviolet light passes and an outflow-side region through which the object after being irradiated with the ultraviolet light passes; and
a retention portion including a first communication portion and a second communication portion, wherein the retention portion is configured to communicate with the inflow-side region through the first communication portion, wherein the inflow-side region communicates with the inflow portion, and wherein the retention portion and the treatment flow path communicate with each other through the second communication portion.
2. The ultraviolet irradiation device according to claim 1, wherein a part of the outer cylinder in contact with the dividing member has an inner diameter smaller than an inner diameter of another part of the outer cylinder.
3. The ultraviolet irradiation device according to claim 1, wherein, in the longitudinal direction, the outer cylinder has an open end on a same side as the at least one open end of the cylindrical portion.
4. The ultraviolet irradiation device according to claim 3, comprising a lid unit configured to cover the at least one open end of the outer cylinder, the lid unit including a first protrusion inserted into a gap between the cylindrical portion and the outer cylinder.
5. The ultraviolet irradiation device according to claim 4, wherein the lid unit includes a second protrusion inside the first protrusion, the first protrusion and the second protrusion being connected to or separated from each other.
6. The ultraviolet irradiation device according to claim 5, wherein the first communication portion includes a plurality of communication holes, the inflow-side region and the retention portion communicating with each other through the first communication portion;
wherein the second protrusion is shorter in height than the first protrusion, and the second protrusion has a tip facing an end face of the cylindrical portion, the first protrusion being formed with a plurality of slits reaching from a tip of the first protrusion halfway through the second protrusion as seen from a side surface of the first protrusion, and a portion of the second protrusion where the first protrusion and the second protrusion overlap being formed with slits overlapping with the slits formed in the first protrusion; and
wherein the plurality of communication holes of the first communication portion are defined by the plurality of slits formed in the first protrusion and the second protrusion.
7. The ultraviolet irradiation device according to claim 4, wherein the light emitting element is provided only at one end portion of the cylindrical portion; and
wherein the one end portion is at an opposite end of the cylindrical portion from where the lid unit is provided.
8. The ultraviolet irradiation device according to claim 1, wherein the retention portion is a circular cylindrical region communicating with the at least one open end of the cylindrical portion and formed on an extension of the cylindrical portion;
wherein the first communication portion includes a plurality of communication holes arranged along a circumferential direction of a side surface of the retention portion; and
wherein the inflow-side region and the retention portion communicate with each other through the first communication portion, in which a total area ratio of a sum of opening areas of the plurality of communication holes included in the first communication portion on the side surface of the retention portion to an area of an entire side surface of the retention portion is from 0.03 to 0.8.
9. The ultraviolet irradiation device according to claim 1, wherein the second communication portion includes one or more plates,
wherein each plate of the one or more plates is formed with a plurality of communication holes opening between front and back surfaces of the plate, and
wherein an opening ratio, defined as a total area per plate of the plurality of communication holes relative to a cross section in a direction perpendicular to a flow in the treatment flow path, is from 0.05 to 0.8.
10. The ultraviolet irradiation device according to claim 9, wherein each plate of the one or more plates are also formed with the communication holes outside a concentric circle having a diameter 0.85 times an inner diameter of the treatment flow path.
11. The ultraviolet irradiation device according to claim 9, wherein radially inner ends of the communication holes formed in outermost circumferences of each plate of the one or more plates are located at a radial position that is less than an inner diameter of the treatment flow path proximate an installation position of the plate, as seen from the longitudinal direction of the treatment flow path.
12. The ultraviolet irradiation device according to claim 1, wherein the outflow-side region communicates with the treatment flow path, and the object after passing through the treatment flow path flows into the outflow-side region.

13. The ultraviolet irradiation device according to claim 1, comprising:
a plurality of communication portions provided in series to each other in the flow path of the object between the inflow portion and the treatment flow path;
wherein the plurality of communication portions includes the first communication portion and the second communication portion included in the retention portion, and
wherein each of the plurality of communication portions includes a plurality of communication holes.

14. The ultraviolet irradiation device according to claim 13, wherein, in one of the first communication portion and the second communication portion, the plurality of communication holes are oriented in a direction intersecting with the longitudinal direction in which the treatment flow path extends.

15. The ultraviolet irradiation device according to claim 13, wherein one of the first communication portion and the second communication portion of the plurality of communication portions includes, in a plane intersecting with the longitudinal direction in which the treatment flow path extends, the plurality of communication holes oriented in a direction intersecting with the plane.

16. The ultraviolet irradiation device according to claim 15, wherein the one of the first communication portion and the second communication portion is a circular plate formed with the plurality of communication holes, and wherein the plurality of communication holes are arranged concentrically.

17. The ultraviolet irradiation device according to claim 13, comprising, immediately before the plurality of communication portions in the flow path of the object between the inflow portion and the treatment flow path, a front chamber configured to communicate with the plurality of communication holes formed in the plurality of communication portion portions.

18. The ultraviolet irradiation device according to claim 13, wherein, in the first communication portion, the plurality of communication holes are oriented in a direction intersecting with the longitudinal direction in which the treatment flow path extends;
wherein the second communication portion is provided on a downstream side of the first communication portion,
wherein, in a plane intersecting with the longitudinal direction in which the treatment flow path extends, the plurality of communication holes in the second communication portion are oriented in a direction intersecting with the plane; and
wherein the retention portion includes a space provided between the first communication portion and the second communication portion, and the space communicates with the plurality of communication holes formed in the first communication portion and the plurality of communication holes formed in the second communication portion.

19. The ultraviolet irradiation device according to claim 18, comprising a lid unit including a circular annular portion facing one end face of the cylindrical portion, wherein the plurality of communication holes in the first communication portion are formed at a tip of the circular annular portion and are defined by a plurality of slits extending in the longitudinal direction of the treatment flow path.

20. The ultraviolet irradiation device according to claim 18, wherein the space retention portion is a cylindrical space formed on an extension of the treatment flow path, and the plurality of communication holes in the first communication portion are arranged side by side at an outer circumference of the retention portion.

21. The ultraviolet irradiation device according to claim 20, wherein immediately before the first communication portion, the inflow-side region is provided to communicate with the plurality of communication holes formed in the first communication portion,
wherein the inflow-side region is formed into a circular annular shape along at least the outer circumference of the retention portion, and
wherein a "pressure loss coefficient average value/number of communication holes" in the plurality of communication holes formed in the first communication portion is 0.5 times or more an "average diameter/(4th power of longitudinal cross section equivalent inner diameter)" of the inflow-side region.

22. The ultraviolet irradiation device according to claim 18, wherein the second communication portion is a circular plate, and wherein the plurality of communication holes formed in the second communication portion are arranged concentrically in the circular plate.

23. The ultraviolet irradiation device according to claim 22, wherein an opening ratio, defined as a total area of the plurality of communication holes in the second communication portion to a cross section in a direction perpendicular to a flow in the treatment flow path, is from 0.05 to 0.8 times.

24. The ultraviolet irradiation device according to claim 22, wherein, in the plate, a portion of the plurality of communication holes are outside a concentric circle having a diameter 0.85 times an inner diameter of the treatment flow path.

25. The ultraviolet irradiation device according to claim 22, wherein a concentric circle passing through radial inner ends of the communication holes formed on an outermost circumference of the plate has a diameter less than an inner diameter of the treatment flow path.

26. The ultraviolet irradiation device according to claim 13, wherein an inflow port of the inflow portion is arranged to be oriented in a direction orthogonal to the cylindrical portion.

27. An ultraviolet irradiation method configured to allow an object to flow from an inflow portion into a treatment flow path formed inside a cylindrical portion having one open end and extending in a longitudinal direction and irradiating the object passing through the treatment flow path with ultraviolet light, the method comprising:
interposing, between an outer circumferential surface of the cylindrical portion and an inner circumferential surface of an outer cylinder accommodating the cylindrical portion, a dividing member including a first portion in contact with the outer circumferential surface of the cylindrical portion and a second portion in contact with the inner circumferential surface of the outer cylinder, wherein the first portion and the second portion are made of an elastic member, and wherein the dividing member divides a space between the outer circumferential surface of the cylindrical portion and the inner circumferential surface of the outer cylinder into two regions;
using one region of the two regions on the open end side of the cylindrical portion as an inflow-side region through which the object before being irradiated with the ultraviolet light passes, and interposing the inflow-side region and a retention portion downstream of the inflow-side region into a flow path of the object from the inflow portion to the treatment flow path; and allowing the object to pass through the inflow-side region and the retention portion and then flow into the treatment flow path.

\* \* \* \* \*